United States Patent
Cassal et al.

[11] Patent Number: 5,215,972
[45] Date of Patent: Jun. 1, 1993

[54] STEROIDS

[75] Inventors: Jean-Marie Cassal, Mulhouse, France; Nigel Gains, Basel, Switzerland; Eva-Maria Gutknecht, Buggingen-Seefelden, Fed. Rep. of Germany; Georges Hirth, Huningue, France; Hans Lengsfeld, Reinach, Switzerland

[73] Assignee: Hoffmann-La Roche Inc., Nutley, N.J.

[21] Appl. No.: 877,297

[22] Filed: May 1, 1992

Related U.S. Application Data

[63] Continuation of Ser. No. 612,342, Nov. 13, 1990, abandoned.

[30] Foreign Application Priority Data

Nov. 22, 1989 [CH] Switzerland .................. 4183/89

[51] Int. Cl.$^5$ .................. A61K 31/58; A61K 31/56; C07J 53/00
[52] U.S. Cl. .................. 514/76; 514/176; 514/182; 540/5; 552/506
[58] Field of Search .................. 514/76, 176, 182; 540/5; 552/544, 547, 506

[56] References Cited

U.S. PATENT DOCUMENTS 4,680,290 7/1987 Cassal .................. 552/506

FOREIGN PATENT DOCUMENTS 34835 3/1981 European Pat. Off. .
135762 8/1984 European Pat. Off. .
88/2479 4/1988 South Africa .

OTHER PUBLICATIONS

Ramirez, et al., Synthesis of Lecithin Analogues by Means of Cyclic Enediol Phosphates Derivatives of 1-Octadecanol and Cholesterol, J. Org. Chem. 43, No. 12, pp. 2331–2333 (1978).
Pharm. Acta. Helv. 33, 1958 349.

Primary Examiner—Marianne M. Cintins
Assistant Examiner—Kimberly Kestler
Attorney, Agent, or Firm—George M. Gould; George W. Johnston; Ellen Ciambrone Coletti

[57] ABSTRACT

Steroids of the formula

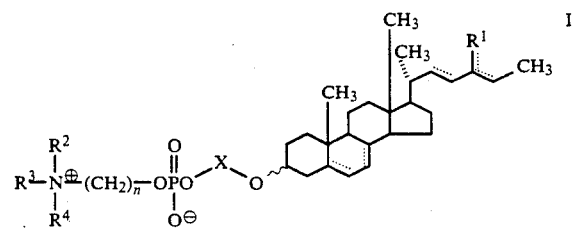

wherein $R^1$ to $R^4$, X and n have the significance given in the description, which lower the intestinal resorption of cholesterol and plasma cholesterol and a process of making same from corresponding steroids having an alcohol residue of the formula —O—X—OH in the 3-position.

32 Claims, No Drawings

STEROIDS

This is a continuation of application Ser. No. 07/612,342 filed Nov. 13, 1990, now abandoned.

BRIEF SUMMARY OF THE INVENTION

The invention relates to novel steroids of the formula

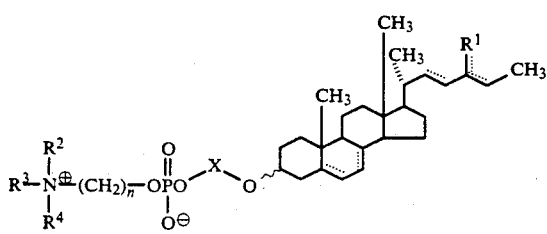

wherein
$R^1$ is hydrogen, lower-alkyl or lower-alkylidene,
$R^2$, $R^3$ and $R^4$ are hydrogen or lower-alkyl or together with the N atom form an unsubstituted or substituted 5- or 6-membered aromatic or saturated heterocyclic group wherein the substituent is lower-alkyl,
n is the number 2, 3 or 4,
X is a group of the formula $-(CH_2)_p-C(Q,Q')-(Z)_{1\ or\ 0}-$, $-CH_2CH(Y)CH_2-(Z)_{1\ or\ 0}-$, $-CH_2CH(CH_2Y)-(Z)_{1\ or\ 0}-$ or $-(CH_2CH_2O)_q-CH_2CH_2-(Z)_{1\ or\ 0}-$, q is the number 1 or 2,
Z is a group of the formula $-C(O)-$, $-OC(O)-$, $-OC(O)CH_2-$, $-OCH_2C(O)-$ or $-N(T)C(O)-$,
Q, Q' and T are hydrogen or lower-alkyl,
p is a whole number between 1 and 9 and, where Z is carbonyl, can also be O,
Y is hydroxy, lower-alkoxy, lower-alkanoyloxy, carbamoyloxy or mono- or di-lower alkyl-carbamoyloxy, the dotted C-C bonds is the 5(6)-, 7(8)-, 22(23)-, 24(25)- and 24(28)-position are optional, whereby the side-chain is either saturated or mono-unsaturated,
and physiologically compatible salts thereof, said compounds are useful in inhibiting the intestinal resorption of cholesterol and lowering plasma cholesterol.

The hydrogen atoms attached to the C atoms in position 3 and 5 of the steroid part of the compounds as set forth in formula I can each independently be in the α- or β-configuration.

DETAILED DESCRIPTION OF THE INVENTION

The invention relates to novel steroids of the formula

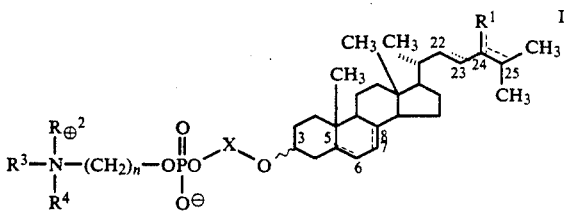

wherein
$R^1$ is hydrogen, lower-alkyl or lower-alkylidene,
$R^2$, $R^3$ and $R^4$ are hydrogen or lower-alkyl or together with the N atom form a 5- or 6-membered aromatic or saturated heterocyclic group which may be lower-alkylated,
n is the number 2, 3 or 4,
X is a group of the formula $-(CH_2)_p-C(Q,Q')-(Z)_{1\ or\ 0}-$, $-CH_2CH(Y)CH_2-(Z)_{1\ or\ 0}-$, $-CH_2CH(CH_2Y)-(Z)_{1\ or\ 0}-$ or $-(CH_2CH_2O)_q-CH_2CH_2-(Z)_{1\ or\ 0}-$, q is the number 1 or 2,
Z is a group of the formula $-C(O)-$, $-OC(O)-$, $-OC(O)CH_2-$, $-OCH_2C(O)-$ or $-N(T)C(O)-$,
Q, Q' and T are hydrogen or lower-alkyl,
p is a whole number between 1 and 9 and, where Z is carbonyl, can also be O,
Y is hydroxy, lower-alkoxy, lower-alkanoyloxy, carbamoyloxy or mono- or di-lower alkyl-carbamoyloxy, the dotted C-C bonds in the 5(6)-, 7(8)-, 22(23)-, 24(25)- and 24(28)-position are optional, whereby the side-chain is either saturated or mono-unsaturated,
and physiologically compatible salts thereof, said compounds are useful in inhibiting the intestinal resorption of cholesterol and lowering plasma cholesterol.

Stated another way, the dotted lines at the 5(6)- and 7(8)-positions can be an additional carbon to carbon bond, and up to one of the dotted lines at the 22(23)-, 24(25)- and 24(28)-positions can be an additional carbon to carbon bond.

The hydrogen atoms attached to the carbon atoms in position 3 and 5 of the steroid part of the compounds as set forth in formula I, can each independently be in the α- or β-configuration.

The invention is also concerned with a process for the preparation of these steroids: medicaments based on these steroids and the use of these steroids as medicaments in mammals; these steroids as pharmaceutically active substances, as well as the use of these steroids in the preparation of medicaments which inhibit the intestinal resorption of cholesterol and which lower the plasma cholesterol.

The term "lower" denotes residues which contain 1 to 7 carbon atoms, preferably up to 4 carbon atoms and can be straight-chain or branched. The term "lower-alkyl" denotes saturated hydrocarbon residues such as methyl, ethyl, n-propyl, isopropyl, n-butyl, t-butyl and the like. The term "lower-alkylidene" denotes radicals derived from an aliphatic hydrocarbon such as methylene, ethylidene and the like. The term "lower-alkanoyloxy" denotes residues such as acetoxy, propionyloxy and the like. The term "lower-alkoxy" denotes alkyl groups attached via an oxygen atom, such as methoxy, ethoxy and the like. The term "heterocyclic" denotes a five or six membered unsubstituted or substituted heterocyclyl which, in addition to ring carbon atoms, can have 1 to 3 hetero atoms selected from the group consisting of nitrogen, oxygen, and sulfur in the ring and which are aromatic, partially saturated or completely saturated, such as pyridinium, N-methylpyrrolidinium, N-methylpiperidinium, pyrazinium, N-methylimidazolium and N-methylmorpholinium, wherein the substituent may be lower alkyl.

Where one of $R^2$, $R^3$ or $R^4$ is hydrogen or lower alkyl, the other two may, taken together with the N atom form a 5- or 6-membered aromatic or saturated heterocyclic group which may be lower-alkylated.

Pharmaceutically acceptable salts of the steroids of formula I are inorganic salts, for example, hydrohalides such as hydrochlorides and sulfates; organic salts; for example, such as trifluoroacetates, mesylates and tosylates; and alkali metal salts for example, such as sodium salts. The compounds of formula I can be present in the form of a zwitterion, that is internal salt. Those compounds in which at least one of the residues $R^2$, $R^3$ and $R^4$ is hydrogen can be present in the form of a hydrogen phosphate.

Among the steroids of formula I there are preferred those in which $R^1$ is hydrogen or lower-alkyl, especially ethyl, those in which $R^2$ is hydrogen or lower-alkyl and $R^3$ and $R^4$ are lower-alkyl, especially methyl, or in which $R^2$, $R^3$ and $R^4$ together with the N atom form a pyridinium or 1-methylpyrrolidinium group.

Further, the steroids of formula I in which n is the number 2, as well as those having a saturated or 5(6)-unsaturated or 5(6)- and 22(23)-unsaturated steroid part are preferred.

Further preferred steroids of formula I are those in which X represents the group —(CH$_2$)$_2$—, —(CH$_2$)$_2$O(CH$_2$)$_2$—, —(CH$_2$)$_2$O(CH$_2$)$_2$O(CH$_2$)$_2$—, —CH$_2$CHOHCH$_2$—, —CH$_2$CH(OCOCH$_3$)CH$_2$—, —CH$_2$CH(OCONHCH$_3$)CH$_2$N[CH(CH$_3$)$_2$]CO—, —(CH$_2$)$_2$NHCO—, —(CH$_2$)$_3$NHCO—, —CH$_2$CHOHCH$_2$OCO—, —(CH(CH$_3$)CO— or especially —(CH$_2$)$_2$OCO—, —(CH$_2$)$_3$OCO—, —(CH$_2$)$_4$OCO—, —(CH$_2$)$_8$OCO—, —(CH$_2$)CO—, —(CH$_2$)$_2$CO—, —(CH$_2$)$_3$CO—, —(CH$_2$)$_5$CO—, —CH$_2$CH(OCOCH$_3$)CH$_2$OCO—, —CH$_2$C(CH$_3$)$_2$CO— or —CH$_2$CH(CH$_2$OH)NHCO—.

The following are examples of preferred compounds of formula I:

0-[[2-[[(Cholest-5-en-3β-yloxy)carbonyl]oxy]ethoxy]-hydroxyphosphinyl]choline hydroxide internal salt, 0-[hydroxy-[3-[(3β-stigmastanyloxy)carbonyl]propoxy]phosphinyl]choline hydroxide internal salt, 0-[[2-(cholest-5-en-3β-yloxy)ethoxy]hydroxyphosphinyl]choline hydroxide internal salt and 0-[hydroxy-[2-[1-(5α-stigmastan-3β-yloxy)formamido]ethoxy]phosphinyl]choline hydroxide internal salt.

The following are further examples of compounds of formula I:

0-[[2-[[(5α-Stigmastan-3β-yloxy)carbonyl]oxy]ethoxy]-hydroxyphosphinyl]choline hydroxide internal salt, 0-[hydroxy-[2-[[(E)-stigmasta-5,22-dien-3β-yloxy]carbonyl]ethoxy]phosphinyl]choline hydroxide internal salt, 0-[[3-[[(cholest-5-en-3β-yloxy)carbonyl]oxy]propoxy]-hydroxyphosphinyl]choline hydroxide internal salt, 0-[[4-[[(cholest-5-en-3β-yloxy)carbonyl]oxy]butoxy]hydroxyphosphinyl]choline hydroxide internal salt, O-[[[8-[[(cholest-5-en-3β-yloxy)carbonyl]oxy]octyl]oxy]hydroxyphosphinyl]choline hydroxide internal salt, O-[[[(cholest-5-en-3β-yloxy)carbonyl]methoxy]hydroxyphosphinyl]choline hydroxide internal salt, O-[[2-[(cholest-5-en-3β-yloxy)carbonyl]ethoxy]hydroxyphosphinyl]choline hydroxide internal salt, O-[hydroxy-[2-[(3β-stigmastanyloxy)carbonyl]ethoxy]phosphinyl]choline hydroxide internal salt, O-[hydroxy-[2-[(stigmasta-5,22-dien-3β-yloxy)carbonyl]ethoxy]phosphinyl]choline hydroxide internal salt, O-[[3-[(cholest-5-en-3β-yloxy)carbonyl]propoxy]hydroxyphosphinyl]choline hydroxide internal salt, O-[hydroxy-[3-[(E)-stigmasta-5,22-dien-3β-yloxy)carbonyl]propoxy]phosphinyl]choline hydroxide internal salt, O-[hydroxy-[[5-[(5α-stigmastan-3β-yloxy)carbonyl]pentyl]oxy]phosphinyl]choline hydroxide internal salt, O-[hydroxy-[[5-[((E)-stigmasta-5,22-dien-3β-yloxy)carbonyl]pentyl]oxy]phosphinyl]choline hydroxide internal salt, O-[hydroxy-[[[(3β-stigmastanyl)oxy]carbonyl]methoxy]phosphinyl]choline hydroxide internal salt, O-[hydroxy-[[[(E)-stigmasta-5,22-dien-3β-yloxy]carbonyl]methoxy]phosphinyl]choline hydroxide internal salt, O-[hydroxy-[2-(stigmasta-5,22-dien-3β-yloxy)ethoxy]phosphinyl]choline hydroxide internal salt, O-[[2-[2-(cholest-5-en-3β-yloxy)ethoxy]ethoxy]hydroxyphosphinyl]choline hydroxide internal salt, O-[hydroxy-[2-[2-[(E)-stigmasta-5,22-dien-3β-yloxy]ethoxy]ethoxy]phosphinyl]choline hydroxide internal salt, O-[[2-[2-[2-(cholest-5-en-3β-yloxy)ethoxy]ethoxy]ethoxy]hydroxyphosphinyl]choline hydroxide internal salt, O-[[2-[(5α-cholestan-3β-yloxy)carbonyloxy]ethoxy]hydroxyphosphinyl]choline hydroxide internal salt, O-[hydroxy-[2-[2-(3β-stigmastanyloxy)ethoxy]ethoxy]phosphinyl]choline hydroxide internal salt, O-[hydroxy-[2-(3β-stigmastanyloxy)ethoxy]phosphinyl]choline hydroxide internal salt, 1-[2-[[hydroxy-[2-[1-(5α-stigmastan-3β-yloxy)formamido]ethoxy]phosphinyl]oxy]ethyl]pyridinium hydroxide internal salt, O-[hydroxy-[2-[1-[(E)-stigmasta-5,22-dien-3β-yloxy]formamido]ethoxy]phosphinyl]choline hydroxide internal salt, O-[hydroxy-[3-[1-[(E)-stigmasta-5,22-dien-3β-yloxy]formamido]propoxy]phosphinyl]choline hydroxide internal salt, O-[hydroxy-[(RS)-3-[N-isopropyl-1-[(E)-stigmasta-5,22-dien-3β-yl]oxyformamido]-2-[(methylcarbamoyl)oxy]propoxy]phosphinyl]choline hydroxide internal salt, O-[[[2-[1-cholest-5-en-3β-yloxy]formamido]ethoxy]hydroxyphosphinyl]choline hydroxide internal salt, O-[[2-[1-(5β-cholestan-3α-yloxy)formamido]ethoxy]-hydroxyphosphinyl]choline hydroxide internal salt, 1-[2-[[hydroxy-[3-[3-[1-(E)-stigmasta-5,22-dien-3β-yloxy]formamido]propoxy]phosphinyl]oxy]ethyl]-pyridinium hydroxide internal salt, O-[hydroxy-[2-[[[(E)-stigmasta-5,22-dien-3β-yloxy]carbonyl]oxy]ethoxy]phosphinyl]choline hydroxide internal salt, 1-[2-[[[2-[1-[cholest-5-en-3β-yloxy]formamido]ethoxy]-hydroxyphosphinyl]oxy]ethyl]-1-methylpyrrolidinium hydroxide internal salt, 1-O-(3α,β-stigmastanyl)-3-O-(RS)-glyceryl-phosphorylcholine, O-[[(RS)-2-acetoxy-3-[5α-stigmastan-3α,β-yloxy]-propoxy]hydroxyphosphonyl]chloline hydroxide internal salt, O-[[(RS)-3-[(cholest-5-en-3β-yloxy)carbonyloxy]-2-hydroxypropoxy]hydroxyphosphinyl]choline hydroxide internal salt, O-[hydroxy-(RS)-2-hydroxy-3-[[5α-stigmastan-3β-yloxy)carbonyloxy]propoxy]phosphinyl]choline hydroxide internal salt O-[hydroxy-[(RS)-2-hydroxy-3-[[(E)-stigmasta-5,22-dien-3β-yloxy]carbonyloxy]propoxy]phosphinyl]-choline hydroxide internal salt, O-[hydroxy-[2-[[(stigmast-5-en-3β-yloxy)carbonyl]oxy]ethoxy]phosphinyl]choline hydroxide internal salt, O-[hydroxy-[3-[(stigmast-5-en-3β-yloxy)carbonyl]-propoxy]phosphinyl]choline hydroxide internal salt, O-[hydroxy-[2-(stigmast-5-en-3β-yloxy)ethoxy]phosphinyl]choline hydroxide internal salt, cholest-5-en-3β-yl 2-[[[2-(dimethylamino)ethoxy]hydroxyphosphinyl]oxy]ethylcarbonate, O-[hydroxy-[2-[1-(stigmast-5-en-3β-yloxy)formamido]ethoxy]phosphinyl]choline hydroxide internal salt, O-[[(RS)-2-acetoxy-3-[[(cholest-5-en-3β-yloxy)carbonyl]oxy]propoxy]hydroxyphosphinyl]choline hydroxide internal salt, O-[[2-[cholest-5-en-3β-yloxy)carbonyl]-2-methylpropoxy]hydroxyphosphinyl]-choline hydroxide internal salt and O-[[(RS)-2-[1-(cholest-5-en-3β-yloxy)formamido]-3-hydroxypropoxy]hydroxyphosphinyl]choline hydroxide internal salt.

The steroids of formula I and the salts thereof can be prepared by a) treating an alcohol of the formula

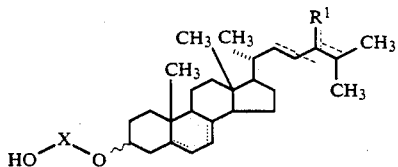

II with intermediary protection of a hydroxy residue Y present in the group X, with an agent which introduces the group of the formula

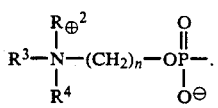

(G)

and b) if desired, hydrogenating an unsaturated steroid of formula I to the saturated steroid, c) if desired, functionally modifying a reactive residue present in the group X of a steroid of formula I, d) if desired, converting a steroid of formula I into a salt.

These reactions can be carried out in a known manner.

Thus, a carbonate of formula II in which X is a group of the formula $-(CH_2)_p-OCO-$ is reacted firstly with a halide of the formula $PO(Hal)_3$, for example, phosphorus oxychloride, in a solvent, such as methylene chloride or chloroform in the presence of a base, such as quinoline or pyridine, at room temperature. The compound obtained can be treated with a salt of the formula

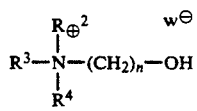

III' wherein W is lower-alkylsulphonyloxy or arylsulphonyloxy, for example, with choline tosylate, in the presence of a base such as pyridine, in a solvent such as methylene chloride at room temperature.

A carbamate of formula II in which X is a group of the formula $-(CH_2)_pN(T)C(O)-$ can be reacted firstly with a halide of the formula

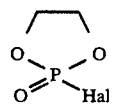

IV for example, with 2-chloro-2-oxo-1,3,2-dioxaphospholane, in a solvent such as tetrahydrofuran (THF) while cooling to temperatures to 0° C. in the presence of a base such as triethylamine. The phosphate obtained can be reacted in the same solvent with an amine of the formula $N(R^2,R^3,R^4)$ while heating, for example, in the range of from about 50° to about 100° C.

An ester of formula II in which X is a group of the formula $-CH(CH_3)CO-$ can firstly be reacted with a halide such as β-bromoethylphosphoric acid dichloride (Pharm. Acta Helv. 33, 1958, 349) in a solvent such as methylene chloride in the presence of a base such as triethylamine. The compound obtained can then be treated in a solvent such as toluene with an amine of the formula $N(R^2,R^3,R^4)$.

As described, for instance, in Example 11 hereinafter, a benzyl group can be used to protect a hydroxy residue Y present in the group X of a compound of formula II. Thus, a glycerol derivative of formula II in which X is a group of the formula $-CH_2CH(OH)CH_2-$ can be reacted with trityl chloride in pyridine to give the corresponding trityl ether. This ether can be converted by means of sodium hydride in THF and benzyl chloride in dimethylformamide (DMF) at a temperature up to 100° C. into the corresponding trityl benzyl diether in which X stands for $-CH_2CH(OCH_2C_6H_5)CH_2-$. After cleavage of the trityl group from the diether, for example, by means of hydrochloric acid in dioxane while heating, the benzyl ether obtained is treated as described above with an agent which introduces the group

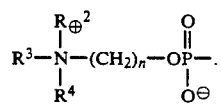

(G)

The glycine derivative of formula I in which X is $-CH_2CH(OH)CH_2-$, which corresponds to the starting compound of formula II, is obtained by cleavage of the benzyl group, for example, by hydrogenation in the presence of palladium-charcoal (Pd/C) in methanol and THF or (in order to avoid the simultaneous hydrogenation of double bonds present in the steroid part of the ether) in the presence of palladium oxide (PdO) in acetic acid.

A benzyl-protected steroid alcohol of formula II in which X stands for $-CH_2CH(OCH_2C_6H_5)CH_2-$ can also be prepared by reacting the corresponding steroid 3-chloroformate with O-benzylglycerol in methylene chloride.

As described, for instance, in Example 22 hereinafter, a phenoxy-carbonyl group can also be used for the protection of a hydroxy residue Y present in the group X of a compound of formula II. Thus, a compound of formula II in which X is a group $-CH_2CH(CH_2OH)NHCO-$ can be reacted with phenyl chloroformate in methylene chloride, THF and pyridine. The resulting compound containing a phenoxycarbonyloxy group is then reacted, for example, in toluene and triethylamine, with an agent which introduces the group of formula G above, for example, with 2-chloro-2-oxo-1,3,2-dioxaphospholane, and then with trimethylamine in toluene and acetonitrile. The compound of formula I in which X is the group $-CH_2CH(CH_2OH)NHCO-$ is then obtained by cleaving off the phenoxycarbonyl group, for example, using aqueous sodium hydroxide.

The hydrogenation of an unsaturated steroid of formula I can be carried out in the presence of Pd/C in a solvent such as methanol at a temperature up to 100° C.

The alkanoylation of a hydroxy group Y can be mentioned as a functional modification of a reactive residue present in the group X of a steroid of formula I. Thus, a glycerol derivative of formula I in which X is the group $-CH_2CH(OH)CH_2-$ can be reacted at room temperature in a solvent such as chloroform in the presence of a base such as pyridine and a catalyst such as dimethylaminopyridine (DMAP) with the carboxylic acid anhydride corresponding to the alkanoyl group to be introduced.

The starting alcohols of formula II in which X is a group of the formula $-(CH_2)_p-C(Q,Q')-Z'$, $-CH_2CH(Y)CH_2-Z'-$, $-CH_2CH(CH_2Y)-Z'-$ or $-(CH_2CH_2O)_q-CH_2CH_2-Z'-$, Z' is a group of the formula $-OC(O)-$, $-OC(O)CH_2-$, $-OCH_2C(O)-$ or $-N(T)C(O)-$ and $R^1$, Q, Q', p, q, y and T have the significance given above are novel and as such are an object of the invention.

The alcohols of formula II can be prepared in a known manner for example, as described in Examples A to M hereinafter.

Thus, an alcohol ether of formula II in which X is for example, a group $-(CH_2)_p-$, can be prepared by reacting the corresponding steroid-3-tosylate with the glycol $HO-(CH_2)_p-OH$ in dioxane at about 120° C.

An alcohol ester of formula II in which X is for example, a group $-(CH_2)_p-CO-$, can be prepared by reacting the corresponding steroid-3-ol in methylene chloride with the corresponding halide of the formula $Hal-(CH_2)_p-COCl$ at about 5° C. in the presence of pyridine and converting the halide obtained into the desired alcohol of formula II by means of potassium trifluoroacetate in methylene chloride, DMF and water at about 80° C.

An alcohol ester of formula II in which X is for example, a group $-CH(CH_3)CO-$, can be prepared by reacting the corresponding steroid-3-ol with lactic acid in toluene in the presence of catalytic amounts of p-toluenesulphonic acid.

An alcohol carbonate of formula II in which X is for example, a group $-(CH_2)_p-OC(O)-$, can be prepared by reacting the corresponding steroid-3-ol in methylene chloride at about $-10°$ C. with a solution of phosgene in toluene and reacting the steroid-3-chloroformate obtained in chloroform or methylene chloride with a diol of the formula $HO-(CH_2)_p-OH$ in the presence of pyridine or triethyl-amine at about 5° C.

An alcohol carbamate of formula II in which X is for example, a group $-(CH_2)_p-N(T)C(O)-$, can be prepared by reacting the corresponding steroid-3-ol in chloroform and THF with phenyl chloroformate in the presence of pyridine and reacting the phenylcarbonate obtained in chloroform with the amine of the formula $HO-(CH_2)_p-N(T)-H$.

A compound of formula II in which X is a group of the formula $-CH_2CH[OCONH(T^1)]CH_2N(T^2)C(O)-$ and $T^1$ and $T^2$ are hydrogen or lower-alkyl can be prepared by reacting the corresponding 1-deoxy-1-amino-3-O-tritylglycerol of the formula $T^2NHCH_2CHOHCH_2OC(C_6H_5)_3$ with a steroid-3-chloroformate in methylene chloride in the presence of potassium hydroxide, reacting the product obtained in methylene chloride with the isocyanate of the formula $O=C=N(T^1)$ at 80° C. and cleaving off the trityl group from the product obtained in dioxan by means of hydrochloric acid at 95° C.

A glycerol derivative of formula II in which X is a group $-CH_2CH(OH)CH_2-$ is obtained by reacting the corresponding 3-O-tosylsteroid in dioxane with glycerol at 100° C.

An alcohol of formula II which has a double bond in the steroid part can be hydrogenated to the corresponding saturated alcohol, for example, in the presence of Pd/C in THF.

The preparation of some compounds of formula II is described in detail in Examples A to M hereinafter.

EXAMPLE A

A solution of 10 g of cholesterol tosylate and 25.3 g of ethylene glycol in 180 ml of dioxan is heated to 120° C. while stirring. The mixture is then treated with 200 ml of water and extracted with ether. The ethereal phase is washed firstly with 10% sodium carbonate solution and then with water. The organic phase is dried and evaporated. The residue is chromatographed on silica gel while eluting with ether/hexane. There are obtained 5.6 g of 2-(cholest-5-en-3β-yloxy)-1-ethanol, m.p. 92°–95° C., the starting material in Example 2q.

EXAMPLE B

In a manner analogous to Example A there are obtained:
a) 2-[[(E)-Stigmasta-5,2-dien-3β-yl]oxy]-1-ethanol, MS: 456 (M+H+),
b) 2-[2-[(E)-stigmasta-5,22-dien-3β-yloxy]ethoxy]-1-ethanol, MS: 501 (M+H+),
c) 2-[2-(cholest-5-en-3β-yloxy)ethoxy]-1-ethanol, MS: 474 (M+H+),
d) 2-[2-[2-(cholest-5-en-3β-yloxy)ethoxy]ethoxy]ethanol, MS: 519 (M+H+).

EXAMPLE C

1. A solution of 20 g of stigmastanol in 200 ml of methylene chloride and 4 ml of pyridine is added dropwise at 5° C. to a solution of 12.5 g of 3-bromopropionyl chloride (obtained from 11.1 g of bromopropionic acid and 9.77 ml of oxalyl chloride in 55 ml of methylene chloride and 3 drops of DMF) in 44 ml of methylene chloride. The mixture is evaporated, the residue is dissolved in 500 ml of methylene chloride and this solution is washed with dilute hydrochloric acid. The organic phase is dried and evaporated. The residue is chromatographed on silica gel while eluting with ether-hexane. There is obtained 3β-stigmastanyl 3-bromopropionate of melting point 150°–152° C.

2. In an analogous manner there are prepared:
a) Stigmasta-5,22-dien-3β-yl 3-bromopropionate,
b) 5α-stigmastan-3β-yl bromoacetate,
c) cholest-5-en-3β-yl bromoacetate,
d) cholest-5-en-3β-yl bromopropionate,
e) 5α-stigmastan-3β-yl 4-bromobutyrate,
f) cholest-5-en-3β-yl 4-chlorobutyrate,
g) 3β-stigmastanyl 4-chlorobutyrate,
h) 3β-stigmastanyl 4-iodobutyrate,
i) (E)-stigmasta-5,22-dien-3β-yl 4-chlorobutyrate,
j) (E)-stigmasta-5,22-dien-3β-yl 4-iodobutyrate,
k) cholest-5-en-3β-yl 4-iodobutyrate,
l) (E)-stigmasta-5,22-dien-3β-yl 6-bromohexanoate,
m) 5α-stigmastan-3β-yl 6-bromohexanoate,
n) stigmast-5-en-3β-yl 4-bromobutyrate.

3. A solution of 23.1 g of 3β-stigmastanyl 3-bromopropionate in 400 ml of methylene chloride and 200 ml of DMF is treated with 63.3 g of potassium trifluoroacetate and heated at 80° C. over 72 hours. After adding 30 ml of water the solution is heated at 80° C. for a further 1 hour. The solution is evaporated and the residue is chromatographed on silica gel using ether-hexane. There is obtained 3β-stigmastanyl 3-hydroxypropionate of melting point 152°–153° C., the starting material of Example 20.

EXAMPLE D

In a manner analogous to Example C there are prepared:
a) Cholest-5-en-3β-yl glycolate, MS: 369 (M—HOCH$_2$COOH),
b) 3β-stigmastanyl glycolate, MS: 399 (M—HOCH$_2$COOH),
c) cholest-5-en-3β-yl 3-hydroxypropionate, MS: 368 (M—HOCH$_2$CH$_2$COOH),
d) stigmasta-5,22-dien-3β-yl 3-hydroxypropionate, MS: 394 (M—HOCH$_2$CH$_2$COOH),
e) cholest-5-en-3β-yl 4-hydroxybutyrate, m.p. 98° C.,
f) 3β-stigmastanyl 4-hydroxybutyrate, m.p. 149° C.,
g) (E)-stigmasta-5,22-dien-3β-yl 4-hydroxybutyrate, m.p. 147° C.,
h) 5α-stigmastan-3β-yl 6-hydroxyhexanoate, m.p. 130° C.,
i) (E)-stigmasta-5,22-dien-3β-yl 6-hydroxyhexanoate, m.p. 133° C.,
j) stigmast-5-en-3β-yl 4-hydroxybutyrate, m.p. 125°–126° C.

EXAMPLE E

A solution of 10 g of cholesteryl chloroformate in 100 ml of methylene chloride and 2.16 ml of pyridine is added dropwise at 5° C. to a solution of 13.8 g of ethylene glycol in 200 ml of methylene chloride. The solution is then treated with 300 ml of water and extracted with methylene chloride. The organic phase is washed with water, dried and evaporated. The residue is recrystallized in methylene chloride-ethanol. There are obtained 6.4 g of cholest-5-en-3β-yl 2-hydroxyethylcarbonate of melting point 139°–140° C., the alcohol starting material of Example 1.

EXAMPLE F

In a manner analogous to Example E there are prepared:
a) 5α-Stigmastan-3β-yl 2-hydroxyethylcarbonate, m.p. 184° C.,
b) 2-hydroxyethyl (E)-stigmasta-5,22-dien-3β-ylcarbonate, m.p. 172° C.,
c) cholest-5-en-3β-yl 3-hydroxypropylcarbonate, m.p. 96° C.,
d) cholest-5-en-3β-yl 4-hydroxybutylcarbonate, m.p. 170° C.,
e) cholest-5-en-3β-yl 8-hydroxyoctylcarbonate, m.p. 79° C.,
f) 2-hydroxyethyl stigmast-5-en-3β-ylcarbonate, m.p. 160° C.

EXAMPLE G

1. A solution of 1.71 g of phenyl chloroformate in 5 ml of CHCl$_3$ is added dropwise to a suspension, cooled to −50° C., of 4.16 g of stigmastanol in 25 ml of CHCl$_3$, 12.5 ml of THF and 0.75 ml of pyridine. A further 0.25 ml of pyridine is then added. The mixture is reacted at a low temperature for 30 minutes and at room temperature for a further 1 hour. The reaction solution is poured into a solution of pyridine and aqueous KHCO$_3$. After the evolution of CO$_2$ has finished the mixture is evaporated to dryness. The residue is partitioned between CH$_2$Cl$_2$ and H$_2$O. After crystallization from CH$_2$Cl$_2$-pentane there are obtained 4.75 g of 3-stigmastanyl phenylcarbonate. M.p. 96° C.

2. 0.3 ml of ethanolamine is added to a solution of 1.07 g of the above phenylcarbonate in 3 ml of CHCl$_3$. The mixture is reacted at room temperature for 2 days. The excess reagent is distilled off and the phenol which results in the reaction is separated as Na phenolate. The compound is crystallized from CH$_2$Cl$_2$. There is obtained 0.9 g of 3β-stigmastanyl (2-hydroxyethyl)carbamate. M.p. 206° C., the starting material in Example 5.

EXAMPLE H

Analogously to Example G,
1. from stigmasterol via (E)-stigmasta-5,22-dien-3β-yl phenylcarbonate, m.p. 156°–157° C., there are obtained:
a) (E)-stigmasta-5,22-dien-3β-yl (2-hydroxyethyl)carbamate, m.p. 187° C., and
b) (E)-stigmasta-5,22-dien-3β-yl (3-hydroxypropyl)carbamate, m.p. 172°–173° C.;

2. from cholesterol via 3β-cholesteryl phenylcarbonate, there is obtained 3β-cholesteryl (2-hydroxyethyl)carbamate, m.p. 168°–170° C.;

3. from epicoprostanol via epicoprostanyl phenylcarbamate, there is obtained epicoprostanyl (2-hydroxyethyl)-carbamate, m.p. 98° C.;

4. from β-sitosterol via stigmast-5-en-3-yl phenylcarbonate, m.p. 108°–109° C., there is obtained stigmast-5-en-3β-yl (2-hydroxyethyl)carbamate, m.p. 198°–199° C., the starting material in Example 19.

EXAMPLE I 1. 10 ml of a 20% phosgene solution in toluene are added to a solution, cooled to −10° C., of 4.12 g of stigmasterol in 40 ml of methylene chloride. The mixture is reacted overnight and then cooled to −10° C. After adding 0.7 ml of triethylamine in 10 ml of methylene chloride the reaction is continued for 24 hours. The mixture is neutralized with 0.7 ml of triethylamine in 10 ml of methylene chloride and the (E)-stigmasta-5,22-dien-3β-yl chloroformate is isolated.

2. A solution of 2.3 g of the above chloroformate in 10 ml of chloroform is added dropwise to a solution, cooled in an ice bath, of 1.6 g of ethylene glycol and 0.5 ml of pyridine in 10 ml of chloroform. The reaction mixture is poured on to ice and a sodium bicarbonate solution. The mixture is extracted with methylene chloride, chromatographed on silica gel with toluene/chloroform/ethyl acetate (4/2/1 vol.). After crystallization from methylene chloride-methanol there are obtained 1.86 g of (E)-stigmasta-5,22-dien-3β-yl (2-hydroxyethyl)carbamate, m.p. 172°–173° C., the alcohol starting material of Example 9.

EXAMPLE J

1. A solution of 1.45 g of 3-O-tosylstigmasterol in 20 ml of dioxane is reacted with 2.5 g of glycerol for 2 hours at 100° C. while stirring. After distillation of the solvent, dilution of the residue with water, extraction with diethyl ether and crystallization from methylene chloride-methanol there is obtained 1 g of O-3α,β-stigmasteryl-glycerol.

2. A solution of 1.7 g of the above product in 15 ml of THF is hydrogenated over 0.5 g of 10% Pd/C under normal pressure. After removal of the catalyst, distillation of the solvent and crystallization from THF-methanol there is obtained in quantitative yield O-3α,β-stigmastanyl-(RS)-glycerol, the starting material of Example 11.

EXAMPLE K 1. 0.74 g of (RS)-glycidol and 2.8 g of trityl chloride in 5 ml of pyridine are reacted overnight. A solution of 2 g of potassium bicarbonate is then added while stirring. After evaporation, partition of the residue between water and methylene chloride and chromatography on silica gel with toluene there are obtained 2.25 g of (RS)-epoxy-1-O-tritylglycerol.

2. 3 g of this product are reacted with 5 ml of isopropylamine in a bomb tube at 100° C. for 2 hours. After distillation of the excess isopropylamine, 4.4 g of (RS)-1-deoxy-1-isopropylamino-3-O-tritylglycerol, m.p. 128°–130° C., are crystallized from methylene chloride-hexane.

3. 1.04 g of the above amine in 20 ml of methylene chloride and 0.2 g of potassium hydroxide in 2 ml of water are added dropwise while stirring to a solution, cooled to −10° C., of 1.1 g of stigmasteryl chloroformate in 4 ml of methylene chloride. After reaction at room temperature for 2 hours, phase separation in a separating funnel, chromatography on silica gel with methylene chloride-diethyl ether (2/1), there are obtained 1.63 g of (E)-stigmasta-5,22-dien-3β-yl isopropyl-[(RS)-2-hydroxy-3-trityloxypropyl]-carbamate, m.p. 75°–76° C.

4. A solution of 2 g of the above product in 10 ml of methylene chloride is reacted with 2 ml of methyl isocyanate in a bomb tube at 80° C. for 40 hours and there is obtained in quantitative yield (E)-stigmasta-5,22-dien-3β-yl isopropyl-[(RS)-2-methylcarbamoyl-3-trityloxypropyl]-carbamate, m.p. 92°–93° C.

5. By cleaving off the trityl group in a manner analogous to Example 11c, there are obtained from 2.5 g of the above trityl ether, 1.7 g of (E)-stigmasta-5,22-dien-3β-yl [(RS)-3-hydroxy-2-[(methylcarbamoyl)oxy]-propyl]-isopropylcarbamate, m.p. 240° C., the starting material in Example 7c.

EXAMPLE L

A solution of 10.2 g of cholesteryl chloroformate in 130 ml of methylene chloride is treated under argon while stirring with 4.6 g of 2-O-benzylglycerol in 120 ml of methylene chloride and 2 ml of pyridine, taken up in 500 ml of water and 50 ml of 1N HCl after 1 hour and extracted with methylene chloride. The organic phase is dried and concentrated at 50° C. After chromatography over SiO$_2$ with n-hexane:ether (1:1) there are obtained 6.17 g of (RS)-2-(benzyloxy)-3-hydroxypropyl chloride 5-en-3β-ylcarbonate, MS: 595 (M+H$^+$), the starting material of Example 13.

EXAMPLE M

A solution of 3.86 g of cholesterol and 0.85 ml of L-(+)-lactic acid (90% in water) in 80 ml of toluene is boiled for 1 hour. The water is separated, the cooled reaction mixture is treated with 0.3 g of p-toluene-sulphonic acid and boiled for a further 4 hours. The reaction mixture is treated with 30 ml of water and extracted with ether. The organic phase is dried over sodium sulphate and concentrated. The residue is purified on silica gel, with petroleum ether/ether 4:1 used as the elution agent. There are obtained 1.5 g of cholest-5-en-3β-yl (S)-2-hydroxypropionate, m.p. 120°–122° C.

The steroids of formula I and the salts thereof inhibit the intestinal resorption of cholesterol.

The inhibition of the intestinal resorption of cholesterol can be demonstrated as follows in an animal experiment:

Squirrel monkeys are orally administered the substances to be investigated together with a test feed containing a protein, starch, triolein and [26-$^{14}$C]-cholesterol. Thereafter, the feces is collected for 2.5 days. The difference between the administered and the collected radioactive cholesterol determined in the feces is taken as the measurement of resorbed cholesterol. The cholesterol resorption (CHORES) is expressed in percentages of the control values determined prior to the medication.

The results which have been obtained with some representative products in accordance with the invention are reproduced in Table I. For each of the compounds indicated in Table I the cholesterol resorption, determined at a dosage of 100 μmol/kg p.o., is given in percentages of the control values determined prior to the medication (pre-period). Moreover, the Table contains data concerning the acute toxicity of the compounds investigated (LD$_{50}$ in mg/kg in the case of single oral or intravenous administration to mice).

TABLE I

| Compound of formula I of Example No. | 2a | 2k | 2q | 2r | 4a |
|---|---|---|---|---|---|
| CHORES in % of the pre-period: | 38 | 39 | 16 | 37 | 30 |
| LD$_{50}$ in mg/kg p.o. | 4000 | 4000 | 4000 | 4000 | |
| i.v. | 250 | 250 | 250 | 500 | |
| Compound of formula I of Example No. | 5 | 6 | 7a | 16 | |
| CHORES in % of the pre-period: | 40 | 31 | 35 | 40 | |
| LD$_{50}$ in mg/kg p.o. | | | 4000 | | |

The products in accordance with the invention can be used as medicaments, in mammals for example, in the form of pharmaceutical preparations. The pharmaceutical preparations are administered orally, for example, in the form of tablets, coated tablets, dragees, hard and soft gelatin capsules, solutions, emulsions or suspensions.

For the preparation of pharmaceutical preparations, the products in accordance with the invention can be mixed with pharmaceutically inert, inorganic or organic carriers. Lactose, maize starch, talc, stearic acid or its salts can be used, for example, as carriers for tablets, coated tablets, dragees and hard gelatine capsules. Vegetable oils, waxes, fats or semi-solid and liquid polyols are, for example, suitable carriers for soft gelatine capsules; depending on the nature of the active substance no carrier is, however, generally required in the case of soft gelatine capsules. Water, polyols, saccharose, invert sugar and glucose are, for example, suitable carriers for the manufacture of solutions and syrups.

The pharmaceutical preparations can, moreover, contain preserving agents, solubilizers, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, medicaments containing a steroid of formula I or a pharmaceutically acceptable salt thereof are also an object of the present invention, as well as a process for the preparation of such medicaments which comprises bringing one or more products in accordance with the invention and, if desired, one or more other therapeutically valuable substances into a galenical administration form. As mentioned earlier, the products in accordance with the invention can be used in the control or prevention of illnesses.

They can be used especially in the control or prevention of hypercholesterolemia and of atherosclerosis. The dosage can vary within wide limits and will, of course, be fitted to the individual requirements in each particular case. In general, in the case of oral administration a daily dosage in the range of from about 50 mg to about 3 g, preferably of from about 200 mg to about 1 g, should be appropriate.

The preparation of compounds of formula I is described in the Examples hereinafter.

EXAMPLE 1

A solution of 48.7 g of cholest-5-en-3β-yl 2-hydroxyethylcarbonate and 10 ml of quinoline in 500 ml of methylene chloride is added dropwise at room temperature to a solution of 12.5 ml of phosphorus oxychloride. The solution is treated at room temperature while stirring with 60 ml of pyridine and 77 g of choline tosylate in 500 ml of methylene chloride, whereupon the reaction mixture is stirred at room temperature overnight. The mixture is treated with 125 ml of water and 34 g of sodium bicarbonate and then with 3000 ml of acetone. The precipitated product is filtered off under suction, dissolved in 1000 ml of chloroform-methanol 1:1 and stirred with 500 g of ion exchanger (Amberlite MB-3). The latter is filtered off under suction and the solution is evaporated. The resulting residue is recrystallized in a mixture of methylene chloride-methanol 1:1 and dioxan. There are obtained 39 g of O-[[2-[[(cholest-5-en-3β-yloxy)carbonyl]oxy]ethoxy]hydroxyphosphinyl]choline hydroxide internal salt of melting point 224° C., MS: 640 (M+H)+.

EXAMPLE 2

In a manner analogous to Example 1, a) starting from 5α-stigmastan-3β-yl 2-hydroxyethylcarbonate there is obtained O-[[2-[[(5α-stigmastan-3β-yloxy)carbonyl]oxy]ethoxy]hydroxyphosphinyl]choline hydroxide internal salt, m.p. 220° C.

b) starting from 2-hydroxyethyl (E)-stigmasta-5,22-dien-3β-ylcarbonate there is obtained O-[hydroxy-[2-[[(E)-stigmasta-5,22-dien-3β-yloxy]carbonyl]ethoxy]-phosphinyl]choline hydroxide internal salt, m.p. 220° C.

c) starting from cholest-5-en-3β-yl 3-hydroxypropylcarbonate there is obtained O-[[3-[[(cholest-5-en-3β-yloxy)carbonyl]oxy]propoxy]hydroxyphosphinyl]choline hydroxide internal salt, m.p. 230° C.

d) starting from cholest-5-en-3β-yl 4-hydroxybutylcarbonate there is obtained O-[[4-[[(cholest-5-en-3β-yloxy)carbonyl]oxy]butoxy]hydroxyphosphinyl]choline hydroxide internal salt, m.p. 232° C.

e) starting from cholest-5-en-3β-yl 8-hydroxyoctylcarbonate there is obtained O-[[[8-[[(cholest-5-en-3β-yloxy)carbonyl]oxy]octyl]oxy]hydroxyphosphinyl]-choline hydroxide internal salt, m.p. 235° C.

f) starting from cholest-5-en-3β-yl glycolate there is obtained O-[[[(cholest-5-en-3β-yloxy)carbonyl]methoxy]hydroxyphosphinyl]choline hydroxide internal salt, m.p. 226° C.

g) starting from cholest-5-en-3β-yl 3-hydroxypropionate there is obtained O-[[2-[(cholest-5-en-3β-yloxy)carbonyl]ethoxy]hydroxyphosphinyl]choline hydroxide internal salt, m.p. 180° C.

h) starting from 3β-stigmastanyl hydroxypropionate there is obtained O-[hydroxy-[2-[(3β-stigmastanyloxy)-carbonyl]ethoxy]phosphinyl]choline hydroxide internal salt, m.p. 187° C.

i) starting from stigmasta-5,22-dien-3β-yl 3-hydroxypropionate there is obtained O-[hydroxy-[2-[(stigmasta-5,22-dien-3β-yloxy)carbonyl]ethoxy]phosphinyl]choline hydroxide internal salt, m.p. 199° C.

j) starting from cholest-5-en-3β-yl 4-hydroxybutyrate there is obtained O-[[3-[(cholest-5-en-3β-yloxy)carbonyl]propoxy]hydroxyphosphinyl]choline hydroxide internal salt, m.p. 255° C.

k) starting from 3β-stigmastanyl 4-hydroxybutyrate there is obtained O-[hydroxy-[3-[(3β-stigmastanyloxy)-carbonyl]propoxy]phosphinyl]choline hydroxide internal salt, m.p. 250° C.

l) starting from (E)-stigmasta-5,22-dien-3β-yl 4-hydroxidebutyrate there is obtained O-[hydroxy-[3-[(E)-stigmasta-5,22-dien-3β-yloxy)carbonyl]propoxy]-phosphinyl]choline hydroxide internal salt, m.p. 225° C.

m) starting from 5α-stigmastan-3β-yl 6-hydroxyhexanoate there is obtained O-[hydroxy-[[5-[(5α-stigmastan-3β-yloxy)carbonyl]pentyl]oxy]phosphinyl]choline hydroxide internal salt, m.p. 254° C.

n) starting from (E)-stigmasta-5,22-dien-3β-yl 6-hydroxyhexanoate there is obtained O-[hydroxy-[[5-[((E)-stigmasta-5,22-dien-3β-yloxy)carbonyl]pentyl]oxy]phosphinyl]choline hydroxide internal salt, m.p. 215° C.

o) starting from 3β-stigmastanyl glycolate there is obtained O-[hydroxy-[[[(3β-stigmastanyl)oxy]carbonyl]methoxy]phosphinyl]choline hydroxide internal salt, m.p. 260° C.

p) starting from (E)-stigmasta-5,22-dien-3βyl-yl glycolate (not isolated) there is obtained O-[hydroxy-[[[(E)-stigmasta-5,22-dien-3β-yloxy]carbonyl]methoxy]phosphinyl]choline hydroxide internal salt, m.p. 215° C.

q) starting from 2-(cholest-5-en-3β-yloxy)-1-ethanol there is obtained O-[[2-(cholest-5-en-3β-yloxy)ethoxy]- hydroxyphosphinyl]choline hydroxide internal salt, MS: 596 (M+H+)

r) starting from 2-[[(E)-stigmasta-5,22-dien-3β-yl]oxy]ethanol there is obtained O-[hydroxy-[2-(stigmasta-5,22-dien-3β-yloxy)ethoxy]phosphinyl]choline hydroxide internal salt, m.p. 230° C.

s) starting from 2-[2-(cholest-5-en-3β-yloxy)ethoxy]-1-ethanol there is obtained O-[[2-[2-(cholest-5-en-3β-yloxy)ethoxy]ethoxy]hydroxyphosphinyl]choline hydroxide internal salt, MS: 640 (M+H+)

t) starting from 2-[2-[(E)-stigmasta-5,22-dien-3β-yloxy]-ethoxy]-1-ethanol there is obtained O-[hydroxy-[2-[2-[(E)-stigmasta-5,22-dien-3β-yloxy]ethoxy]phosphinyl]-choline hydroxide internal salt, MS: 666 (M+H+)

u) starting from 2-[2-[2-(cholest-5-en-3β-yloxy)ethoxy]ethoxy]-ethanol there is obtained O-[[2-[2-[2-(cholest-5-en-3β-yloxy)ethoxy]ethoxy]ethoxy]hydroxyphosphinyl]choline hydroxide internal salt, MS: 684 (M+H+).

EXAMPLE 3

1 g of O-[[2-[(cholest-5-en-3β-yloxy)carbonyloxy]ethoxy]hydroxyphosphinyl]choline hydroxide internal salt is hydrogenated in 100 ml of methanol with 1 g of Pd/C 5% under 30 bar of $H_2$ at 80° C. After filtration the solution is evaporated and the residue is dissolved in chloroform-methanol-dioxan. By adding ether there is obtained 0.6 g of O-[[2-[(5α-cholestan-3β-yloxy)carbonyloxy]ethoxy]hydroxyphosphinyl]choline hydroxide internal salt as a hygroscopic powder, m.p. 225° C.

EXAMPLE 4

In a manner analogous to Example 3, a) using O-[hydroxy-[2-[2-[(E)-stigmasta-5,22-dien-3β-yloxy]ethoxy]ethoxy]phosphinyl]choline hydroxide internal salt there is obtained O-[hydroxy-[2-[2-(3β-stigmastanyloxy)ethoxy]ethoxy]phosphinyl]choline hydroxide internal salt, MS: 670 (M+H+)

b) using O-[hydroxy-[2-(stigmasta-5,22-dien-3β-yloxy)ethoxy]phosphinyl]choline hydroxide internal salt there is obtained O-[hydroxy-[2-(3β-stigmastanyloxy)ethoxy]phosphinyl]choline hydroxide internal salt, m.p. 200° C.

EXAMPLE 5

1 g of 3β-stigmastanyl (2-hydroxyethyl)carbamate and 0.35 ml of Et₃N are dissolved in 5 ml of THF. A solution of 315 mg of 2-chloro-2-oxo-1,3,2-dioxaphospholane in 3 ml of THF is added dropwise to the solution, which is cooled in an ice bath. The suspension obtained is stirred at room temperature for 5 hours. The Et₃N.HCl precipitate is then filtered off and the solution remaining behind is evaporated.

The phosphate obtained is dissolved in 10 ml of THF, the solution is treated in a pressure flask with 1 g of (CH₃)₃N in 10 ml of THF. The mixture is reacted at 70° C. for 24 hours. After distillation of the excess reagent and of the solvent the residue is taken up in 20 ml of MeOH-CHCl₃ and the solution is percolated through an ion exchanger (Amberlite MB3). The product is chromatographed on silica gel with CHCl₃—MeOH—H₂O (60/35/5 in vol.). There is obtained 0.6 g of O-[hydroxy-[2-[1-(5α-stigmastan-3β-yloxy)formamido]ethoxy]phosphinyl]choline hydroxide internal salt, MS: 669 (M+H+).

EXAMPLE 6

The preparation of the phosphate is repeated as described in Example 5. The material obtained from 2 mmol of starting carbamate is dissolved in 5 ml of dry pyridine and reacted at 80° C. for 24 hours. The product is isolated and purified analogously to Example 5. There is obtained 0.95 g of 1-[2-[[hydroxy-[2-[1-(5α-stigmastan-3β-yloxy)-formamido]ethoxy]phosphinyl]oxy]ethyl]pyridinum hydroxide internal salt, MS: 689 (M+H+).

EXAMPLE 7

In a manner analogous to Example 5, a) starting from (E)-stigmasta-5,22-dien-3β-yl (2-hydroxyethyl)carbamate there is obtained O-[hydroxy-[2-[1-[(E)-stigmasta-5,22-dien-3β-yloxy]formamido]ethoxy]phosphinyl]choline hydroxide internal salt, MS: 665 (M+H+)

b) starting from (E)-stigmasta-5,22-dien-3β-yl (3-hydroxypropyl)carbamate there is obtained O-[hydroxy-[3-[1-[(E)-stigmasta-5,22-dien-3β-yloxy]formamido]propoxy]phosphinyl]choline hydroxide internal salt, MS: 679 (M+H+)

c) starting from (E)-stigmasta-5,22-dien-3β-yl [(RS)-3-hydroxy-2-[(methylcarbamoyl)oxy]propyl]-isopropylcarbamate there is obtained O-[hydroxy-[(RS)-3-[N-isopropyl-1-[(E)-stigmasta-5,22-dien-3β-yl]oxyformamido]-2-[(methylcarbamoyl)oxy]propoxy]phosphinyl]choline hydroxide internal salt, MS: 794 (M+H+)

d) starting from 3β-cholesteryl (2-hydroxyethyl)carbamate there is obtained O-[[[2-[1-cholest-5-en-3β-yloxy]formamido]ethoxy]hydroxyphosphinyl]choline hydroxide internal salt, MS: 639 (M+H+)

e) starting from epicoprostanyl (2-hydroxyethyl)carbamate there is obtained O-[[2-[1-(5β-cholestan-3α-yloxy)formamido]ethoxy]hydroxyphosphinyl]choline hydroxide internal salt, MS: 641 (M+H+).

EXAMPLE 8

In a manner analogous to Example 6, starting from (E)-stigmasta-5,22-dien-3β-yl (3-hydroxypropyl)carbamate there is obtained 1-[2-[[hydroxy-[3-[1-[(E)-stigmasta-5,22-dien-3β-yloxy]formamido]propoxy]phosphinyl]oxy]ethyl]pyridinium hydroxide internal salt, MS: 699 (M+H+).

EXAMPLE 9

A solution of 2.22 g of (E)-stigmasta-5,22-dien-3β-yl (2-hydroxyethyl)carbonate and 1.1 ml of pyridine in 10 ml of chloroform is added dropwise to a solution, cooled to 0° C., of 0.75 g of phosphorus oxychloride in 3 ml of chloroform. The mixture is reacted at room temperature for 1 hour. Then, 1.6 g of choline tosylate in 15 ml of pyridine are added. The mixture is stirred overnight, then a solution of 2 g of potassium bicarbonate is added. The mixture is evaporated to dryness and the residue is taken up in 100 ml of THF/methanol/chloroform (1/1/1). The solids are filtered off. The solution remaining behind is percolated over an ion exchanger (Amberlite MB-3). After chromatography on silica gel with chloroform/methanol/water (60/35/5 vol) and crystallization from methylene chloride/acetone there are obtained 1.6 g of O-[hydroxy-[2-[[[(E)-stigmasta-5,22-dien-3β-yloxy]carbonyl]oxy]ethoxy]phosphinyl]choline hydroxide internal salt, MS: 666 (M+H+).

EXAMPLE 10

4.75 g of 3β-cholesteryl (2-hydroxyethyl)carbamate are reacted with 2-chloro-2-oxo-1,3,2-dioxaphospholane. The phosphate obtained is treated with N-methylpyrrolidine at 70° C. for 24 hours. After chromatography on silica gel with chloroform/methanol/water (30/62.5/7.5 vol.) there are obtained 1.2 g of 1-[2-[[[2-[1-[cholest-5-en-3β-yloxy]formamido]ethoxy]hydroxyphosphinyl]oxy]ethyl]-1-methylpyrrolidinium hydroxide internal salt, MS: 665 (M+H+).

EXAMPLE 11 a) 1.41 g of trityl chloride are added to a solution of 2.49 g of O-3α,β-stigmastanyl-(RS)-glycerol in 10 ml of pyridine. After reaction for 48 hours a potassium bicarbonate solution is added while stirring. The mixture is evaporated to dryness. The residue is partitioned between methylene chloride and water. After chromatography on silica gel with methylene chloride there is obtained 1-O-trityl-3-O-(3α,β-stigmastanyl)-(RS)-glycerol.

b) 2.4 g of the above trityl ether in 10 ml of THF and then 0.46 ml of benzyl chloride in 5 ml of DMF are added dropwise to a suspension of 96 mg of sodium hydride in 5 ml of THF. After reaction at 80° C. for 2 hours, distillation of the solvent and partition of the residue between methylene chloride and water there is obtained 1-O-trityl-2-O-benzyl-3-O-(3α,β-stigmastanyl)-(RS)-glycerol.

c) 2 ml of 1N hydrochloric acid are added to a solution, heated to 95° C., of 2.4 g of the above benzyl ether in 20 ml of dioxan. After reaction at 95° C. for 2 hours the solvent is distilled off, the residue is taken up in hexane and the precipitated triphenylmethanol is separated. After chromatography on silica gel with toluene/ethyl acetate (9/1) there are obtained 1.5 g of 1-O-(3α,β-stigmastanyl)-2-O-benzyl-(RS)-glycerol.

d) In a manner analogous to Example 5, from 1.4 g of the above glycerol derivative, firstly by reaction with 2-chloro-2-oxo-1,3,2-dioxapholane and then by reaction of the resulting phosphate with trimethylamine, there is obtained 0.8 g of 1-O-(3α,β-stigmastanyl)-2-O-benzyl-3-O-(RS)-glyceryl-phosphorylcholine, MS: 746 (M+H+).

e) A solution of 0.77 g of the above benzyl ether in 10 ml of methanol and 5 ml of THF is hydrogenated under normal pressure in the presence of 10% Pd/C. There is obtained in quantitative yield 1-O-(3α,β-stigmastanyl)-3-O-(RS)-glyceryl-phosphorylcholine, MS: 656 (M+H+).

EXAMPLE 12

50 mg of DMAP and 0.5 ml of acetic anhydride are added to a solution of 0.5 g of the glycerol derivative of Example 11 in 3 ml of chloroform and 1 ml of pyridine. After reaction for 1 hour the mixture is concentrated to dryness. The solution of the residue in 20 ml of methanol is percolated over ion exchanger (Amberlite MB-3). There is obtained 0.51 g of O-[[(RS)-2-acetoxy-3-[5α-stigmastan-3α,β-yloxy]propoxy]hydroxyphosphonyl]-choline hydroxide internal salt, MS: 698 (M+H+).

EXAMPLE 13 a) 1.15 ml of phosphorus oxychloride are treated under argon and while stirring with 6.1 g of (RS)-2-(benzyloxy)-3-hydroxypropylcholest-5-en-3β-yl carbonate and 1.5 ml of quinoline in 80 ml of methylene chloride. After 4 hours 7.4 g of choline tosylate and 6 ml of pyridine is added thereto and after 24 hours 15 ml of water and 4 g of NaHCO₃ is added. After 30 minutes the mixture is poured into 500 ml of water and 50 ml of 1N HCl and extracted with chloroform. The organic phase is concentrated. The product is dissolved in 150 ml of MeOH-CHCl₃ (2:1) and treated with 100 g of ion exchanger (Amberlit MB3). After stirring for 16 hours the ion exchanger is filtered off under suction. The solution obtained is concentrated at 60° C., distilled with toluene and dried. The residue is purified over silica gel with CHCl₃—MeOH (1:1) and CHCl₃—MeOH—H₂O (60:35:5). After drying there are obtained 4.9 g of O-[[(RS)-2-benzyloxy-3-[(cholest-5-en-3β-yloxy)carbonyloxy]propoxy]hydroxyphosphinyl]choline hydroxide internal salt, yield: 63%. MS: 760 (M+H+).

b) 4.65 g of the product of a) and 1.4 g of PdO in 200 ml of CH₃COOH are stirred under H₂ under normal pressure for 20 minutes. After filtration of the catalyst the solution is concentrated at 60° C. The residue is washed in 200 ml of ether, filtered and dried. The residue is dissolved in 40 ml of CHCl₃—MeOH (1:1) and treated with 25 ml of dioxan and 200 ml of ether. The separated crystals are filtered off under suction, washed with ether and dried at 50° C. There are obtained 3.25 g of O-[[(RS)-3-[(cholest-5-en-3β-yloxy)carbonyloxy]-2-hydroxypropoxy]hydroxyphosphinyl]choline hydroxide internal salt (strongly hygroscopic), yield: 79%, MS: 670 (M+H+).

EXAMPLE 14

In a manner analogous to Example 13 there can be manufactured:

a) O-[Hydroxy-(RS)-2-hydroxy-3-[[5α-stigmastan-3β-yloxy)carbonyloxy]propoxy]phosphinyl]choline hydroxide internal salt (epimers 1:1), MS: 700 (M+H+)

b) O-[hydroxy-[(RS)-2-hydroxy-3-[[(E)-stigmasta-5,22-dien-3β-yloxy]carbonyloxy]propoxy]phosphinyl]-choline hydroxide internal salt (epimers 1:1), MS: 696 (M+H+).

EXAMPLE 15 a) A solution of 1 g of cholest-5-en-3β-yl (S)-2-hydroxypropionate and 0.37 ml of triethylamine in 5 ml of methylene chloride is added dropwise to a solution of 1 g of β-bromoethyl-phosphoric acid dichloride in 10 ml of methylene chloride. The mixture is stirred firstly at room temperature for 4 hours, then under reflux for 1 hour. After adding 5 ml of water the mixture is boiled at reflux for 2 hours. The mixture is diluted with methylene chloride, the aqueous phase is separated, the organic phase is washed with water, dried over sodium sulphate and concentrated. The residue is dissolved in ether and treated with a solution of 5 g of barium acetate in 20 ml of water. The mixture is stirred at room temperature for 20 hours, the resulting barium salt is filtered off and is treated with a mixture of 20 ml of 3N hydrochloric acid and 20 ml of methylene chloride. The mixture is stirred at room temperature for 1 hour, the organic phase is separated, dried over sodium sulphate and concentrated. There is obtained 0.7 g of cholest-5-en-3β-yl (S)-2-[[(2-bromoethoxy)hydroxphosphinyl]oxy]propionate, MS: 643 (M-H)−.

b) A solution of 0.7 g of cholest-5-en-3β-yl (S)-2-[[(2-bromoethoxy)hydroxyphosphinyl]oxy]propionate in 15 ml of toluene is treated with 15 ml of trimethylamine in a dry-ice bath. The mixture is heated to 60° C. for 30 hours. After cooling the reaction mixture is taken up in toluene and concentrated. The residue is taken up in 30 ml of methanol, treated with 2 g of silver carbonate and stirred at 50° C. for 0.5 hour. The precipitate is filtered off, concentrated and there is obtained 0.6 g of O-[[(S)-1-[(cholest-5-en-3β-yloxy)carbonyl]ethoxy]hydroxyphosphinyl]choline hydroxide internal salt, MS: 624 (M+H+).

EXAMPLE 16

In a manner analogous to Example 1, starting from stigmast-5-en-3β-yl 2-hydroxyethylcarbonate, there is obtained O-[hydroxy-[2-[[(stigmast-5-en-3β-yloxy) carbonyl]oxy]ethoxy]-phosphinyl]choline hydroxide internal salt, m.p. 207° C. (decomposition).

EXAMPLE 17

In manner analogous to Example 2k) and Example 2q), there are respectively obtained
 a) O-[hydroxy-[3-[(stigmast-5-en-3β-yloxy)carbonyl]propoxy]phosphinyl]choline hydroxide internal salt, m.p. 220° C. (decomposition), and
 b) O-[hydroxy-[2-(stigmast-5-en-3β-yloxy)ethoxy]-phosphinyl]choline hydroxide internal salt, m.p. 197° C. (decomposition).

EXAMPLE 18

In a manner analogous to Example 5, but using dimethylamine in place of triethylamine, there is obtained cholest-5-en-3β-yl 2-[[[2-(dimethylamino)ethoxy]hydroxyphosphinyl]oxy]ethylcarbonate, m.p. 150° C. (decomposition).

EXAMPLE 19

In a manner analogous to Example 5, there is obtained O-[hydroxy-[2-[1-(stigmast-5-en-3β-yloxy)formamido]ethoxy]phosphinyl]choline hydroxide internal salt, m.p. 225° C. (decomposition).

EXAMPLE 20

In a manner analogous to Example 12, there is obtained O-[[(RS)-2-acetoxy-3-[[(cholest-5-en-3β-yloxy)carbonyl]oxy]propoxy]hydroxyphosphinyl]choline hydroxide internal salt, m.p. 130° C. (decomposition).

EXAMPLE 21 a) A solution of 11.6 g of cholesterol and 3.6 g of hydroxypivalic acid in 80 ml of toluene is treated with 1 g of p-toluenesulphonic acid and boiled for 4 hours. The reaction mixture is treated with water and extracted with ether. The organic phase is dried and concentrated and the residue is purified over silica gel with petroleum ether/ether (4:1). There are obtained 1.9 g of cholest-5-en-3β-yl 3-hydroxy-2,2-dimethyl-propionate, m.p. 174°–176° C.

b) To a solution of 1.9 g of the product of a) in 60 ml of methylene chloride are added dropwise firstly 1.1 ml of triethylamine and then a solution of 1.42 g of β-bromoethyl-phosphoric acid dichloride in 30 ml of methylene chloride. The mixture is boiled under reflux for 18 hours, and, after the addition of water, boiled under reflux for 1 hour. The aqueous phase is separated and the organic phase is washed with water, dried and concentrated. The residue is dissolved in ether and treated with a solution of 15 g of barium acetate in 30 ml of water. The mixture is stirred for 20 hours, the resulting barium salt is filtered off and treated with a mixture of 50 ml of 3N hydrochloric acid and 50 ml of methylene chloride. The mixture is stirred at room temperature for 1 hour and the organic phase is separated, dried and concentrated. There are obtained 1.6 g of cholest-5-en-3β-yl 3-[[(2-bromoethoxy)hydroxy-phosphinyl]oxy]-2,2-dimethylpropionate, m.p. 98° C.

c) A solution of 1.6 g of the product of b) in 15 ml of toluene is treated with 15 ml of trimethylamine while cooling in a dry-ice bath. The mixture is heated to 60° C. for 2 days. After cooling in a dry-ice bath the reaction mixture is taken up in toluene and concentrated. The residue is taken up in methanol, treated with 3 g of silver carbonate and stirred at 50° C. for 0.5 hour. The precipitate is filtered off and the filtrate is concentrated. By recrystallization of the residue from ether there is obtained 0.8 g (52%) of O-[[2-[cholest-5-en-3β-yloxy)-carbonyl]-2-methylpropoxy]hydroxyphosphinyl]choline hydroxide internal salt, m.p. 210° C.

EXAMPLE 22 a) A solution of 5.00 g of cholesteryl chloroformate in 20 ml of methylene chloride is added dropwise to a mixture of 1.4 g of DL-serinol.HCl and 3.1 ml of triethylamine in 30 ml of methylene choride. After stirring for 45 hours the mixture is taken up in aqueous methanol and extracted with chloroform. The organic phase is dried and concentrated. After chromatography over $SiO_2$ with chloroform and then with ether there are obtained 4.3 g of cholest-5-en-3β-yl [2-hydroxy-1-(hydroxymethyl)ethyl]carbamate, m.p. 158° C. (decomposition). b) A solution of 3.7 g of the product of a) in 30 ml of methylene chloride, 10 ml of THF and 0.6 ml of pyridine is treated under argon with 1 ml of phenyl chloroformate in 15 ml of methylene chloride. After stirring for 1 hour the solution is taken up in 200 ml of water and 50 ml of 0.1N HCl and extracted with 150 ml of methylene chloride. The organic phase is dried and concentrated. After chromatography over $SiO_2$ with n-hexane/ether (1:1) and ether there are obtained 2.1 g of cholest-5-en-3β-yl [(RS)-2-hydroxy-1-[(phenoxycarbonyl)oxymethyl]ethyl]carbamate.

c) 0.05 ml of 2-chloro-2-oxo-1,3,2-dioxaphospholane is added to a mixture of 320 mg of the product of b) in 20 ml of toluene and 0.08 ml of triethylamine under argon while stirring at room temperature. The $(Et)_3N:HCl$ is filtered off under suction after 16 hours. The solution obtained is concentrated and the residue is dissolved in a solution of 2 g of trimethylamine in 20 ml of toluene and 5 ml of acetonitrile and held at 80° C. The solution is concentrated after 6 hours. The product, O-[[(RS)-2-[1-(cholest-5-en-3β-yloxy)formamido]-3-(phenoxycarbonyloxy)propoxy]hydroxyphosphinyl]-choline hydroxide internal salt, is used in the next step without purification.

d) The product of c) is dissolved in 20 ml of methanol-chloroform (1:1) and treated with 2 ml of 1N NaOH at room temperature while stirring. After adding 10 g of ion exchanger (Amberlite MB-3) and stirring for 4 hours the solution is concentrated, azeotropically distilled with toluene and then dried. The residue is chromatographed on silica gel with $CHCl_3$—MeOH—$H_2O$ (60/35/5 by vol.). After drying there are obtained 200 mg of O-[[(RS)-2-[1-(cholest-5-en-3β-yloxy)formamido]-3-hydroxypropoxy]hydroxyphosphinyl]choline hydroxide internal salt, m.p. 220° C. (decomposition).

Tablets and capsules of the following composition are prepared in a known manner:

EXAMPLE a

| Tablets | 1 tablet contains |
|---|---|
| O-[Hydroxy-[3-[(3β-stigmastanyloxy)-carbonyl]propoxy]phosphinyl]choline hydroxide internal salt | 200 mg |
| Microcrystalline cellulose | 155 mg |
| Maize starch | 25 mg |
| Talc | 25 mg |
| Hydroxypropylmethylcellulose | 20 mg |
| | 425 mg |

EXAMPLE b

| Capsules | 1 capsule contains |
|---|---|
| O-[Hydroxy-[3-[(3β-stigmastanyloxy)-carbonyl]propoxy]phosphinyl]choline hydroxide internal salt | 100.0 mg |
| Maize starch | 20.0 mg |
| Lactose | 95.0 mg |
| Talc | 4.5 mg |
| Magnesium stearate | 0.5 mg |
| | 200.0 mg |

We claim:

1. A compound of the formula

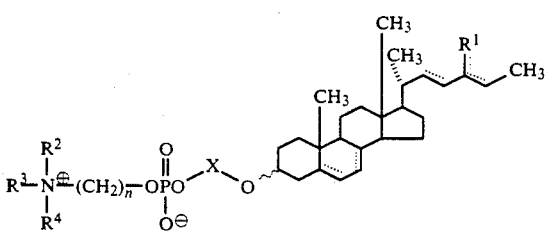

wherein $R^1$ is hydrogen, lower-alkyl or lower-alkylidene, $R^2$, $R^3$ and $R^4$ are hydrogen or lower-alkyl or together with the N atom form a 5- or 6-membered aromatic or saturated heterocyclic group which may be lower-alkylated, n is the number 2, 3 or 4, X is a group of the formula $-(CH_2)_p-C(Q,Q')-(Z)_{1\ or\ 0}-$, $-CH_2CH(Y)CH_2-(Z)_{1\ or\ 0}-$, $-CH_2CH(CH_2Y)-(Z)_{1\ or\ 0}-$ or $-(CH_2CH_2O)_q-CH_2CH_2-(Z)_{1\ or\ 0}-$, q is the number 1 or 2, Z is a group of the formula $-C(O)-$, $-OC(O)-$, $-OC(O)CH_2-$, $-OCH_2C(O)-$ or $-N(T)-C(O)-$, Q, Q' and T are hydrogen or lower-alkyl, p is a whole number between 1 and 9 and, where Z is carbonyl, can also be O, Y is hydroxy, lower-alkoxy, lower-alkanoyloxy, carbamoyloxy or mono- or di-lower alkyl-carbamoyloxy, wherein the dotted lines at the 5(6)-, 7(8)-positions can be an additional carbon to carbon bond, and up to one of the dotted lines at the 22(23)-, 24(25)- or 24(28)-positions can be an additional carbon to carbon bond, and physiologically compatible salts thereof.

2. A compound according to claim 1, wherein $R^1$ is hydrogen or lower-alkyl.

3. A compound according to claim 2, wherein $R^1$ is ethyl.

4. A compound according to claim 2, wherein $R^2$ is hydrogen or lower-alkyl and $R^3$ and $R^4$ are lower-alkyl.

5. A compound according to claim 4, wherein $R^2$, $R^3$ and $R^4$ are methyl.

6. A compound according to claim 2, wherein $R^2$, $R^3$ and $R^4$ together with the N atom form a pyridinium or 1-methylpyrrolidinium group.

7. A compound according to claim 1, wherein n is the number 2.

8. A compound according to claim 1 having a 5(6)-unsaturated or 5(6)- and 22(33)-unsaturated steriod part.

9. A compound according to claim 1, wherein X is the group $-(CH_2)_2-$, $-(CH_2)_2O(CH_2)_2-$, $-(CH_2)_2O(CH_2)_2O(CH_2)_2-$, $-CH_2CHOHCH_2-$, $-CH_2CH(OCOCH_3)CH_2-$, $-CH_2CH(OCONHCH_3)CH_2N[CH(CH_3)_2]CO-$, $-(CH_2)_2NHCO-$, $-(CH_2)_3NHCO-$, $-CH_2CHOHCH_2OCO-$, $-(CH(CH_3)CO-$, $-(CH_2)_2OCO-$, $-(CH_2)_3OCO-$, $-(CH_2)_4OCO-$, $-(CH_2)_8OCO-$, $-(CH_2)CO-$, $-(CH_2)_2CO-$, $-(CH_2)_3CO-$, $-(CH_2)_5CO-$, $-CH_2CH(OCOCH_3)CH_2OCO-$, $-CH_2C(CH_3)_2CO-$ or $-CH_2CH(CH_2OH)NHCO-$.

10. A compound according to claim 1 selected from the group consisting of

O-[[2-[[(Cholest-5-en-3β-yloxy)carbonyl]oxy]ethoxy]hydroxyphosphinyl]choline hydroxide internal salt, O-[hydroxy-[3-[(3β-stigmastanyloxy)carbonyl]propoxy]phosphinyl]choline hydroxide internal salt, O-[[2-(cholest-5-en-3β-yloxy)ethoxy]hydroxyphosphinyl]choline hydroxide internal salt and O-[hydroxy-[2-[1-(5α-stigmastan-3β-yloxy)formamido]ethoxy]phosphinyl]choline hydroxide internal salt.

11. A compound according to claim 1 selected from the group consisting of

O-[[2-[[(5α-Stigmastan-3β-yloxy)carbonyl]oxy]ethoxy]hydroxyphosphinyl]choline hydroxide internal salt, O-[hydroxy-[2-[[[E)-stigmasta-5,22-dien-3β-yloxy]carbonyl]ethoxy]phosphinyl]choline hydroxide internal salt, O-[[3-[[(cholest-5en-3β-yloxy)carbonyl]oxy]propoxy]hydroxyphosphinyl]choline hydroxide internal salt, O-[[4-[[(cholest-5-en-3β-yloxy)carbonyl]oxy]butoxy]hydroxyphosphinyl]choline hydroxide internal salt, O-[[[8-[[(cholest-5-en-3β-yloxy)carbonyl]oxy]octyl]oxy]hydroxyphosphinyl]choline hydroxide internal salt, O-[[[(cholest-5-en-3β-yloxy)carbonyl]methoxy]hydroxyphosphinyl]choline hydroxide internal salt, O-[[2-[(cholest-5-en-3β-yloxy)carbonyl]ethoxy]hydroxyphosphinyl]choline hydroxide internal salt, O-[hydroxy-[2-[(3β-stigmastanyloxy)carbonyl]ethoxy]phosphinyl]choline hydroxide internal salt, O-[hydroxy-[2-[(stigmasta-5,22-dien-3β-yloxy)carbonyl]ethoxy]phosphinyl]choline hydroxide internal salt, O-[[3-[(cholest-5-en-3β-yloxy)carbonyl]propoxy]hydroxyphosphinyl]choline hydroxide internal salt, O-[hydroxy-[3-[(E)-stigmasta-5,22-dien-3β-yloxy)carbonyl]propoxy]phosphinyl]choline hydroxide internal salt, O-[hydroxy-[[5-[(5α-stigmastan-3β-yloxy)carbonyl]pentyl]oxy]phosphinyl]choline hydroxide internal salt, O-[hydroxy-[[5-[((E)-stigmasta-5,22-dien-3β-yloxy)carbonyl]pentyl]oxy]phosphinyl]choline hydroxide internal salt, O-[hydroxy-[[[(3β-stigmastanyl)oxy]carbonyl]methoxy]phosphinyl]choline hydroxide internal salt, O-[hydroxy-[[[(E)-stigmasta-5,22-dien-3β-yloxy]carbonyl]methoxy]phosphinyl]choline hydroxide internal salt, O-[hydroxy-[2-(stigmasta-5,22-dien-3β-yloxy)ethoxy]phosphinyl]choline hydroxide internal salt, O-[[2-[2-(cholest-5-en-3β-yloxy)ethoxy]ethoxy]hydroxyphosphinyl]choline hydroxide internal salt, O-[hydroxy-[2-[2-[(E)-stigmasta-5,22-dien-3β-yloxy]ethoxy]ethoxy]phosphinyl]choline hydroxide internal salt, O-[[2-[2-[2-(cholest-5-en-3β-yloxy)ethoxy]ethoxy]ethoxy]hydroxyphosphinyl]choline hydroxide internal salt, O-[[2-[(5α-cholestan-3β-yloxy)carbonyloxy]ethoxy]hydroxyphosphinyl]choline hydroxide internal salt, O-[hydroxy-[2-[2-(3β-stigmastanyloxy)ethoxy]ethoxy]phosphinyl]choline hydroxide internal salt, O-[hydroxy-[2-(3β-stigmastanyloxy)ethoxy]phosphinyl]choline hydroxide internal salt, 1-[2-[[hydroxy-[2-[1-(5α-stigmastan-3β-yloxy)formamido]ethoxy]phosphinyl]oxy]ethyl]pyridinium-hydroxide internal salt, O-[hydroxy-[2-[1-[(E)-stigmasta-5,22-dien-3β-yloxy]formamido]ethoxy]phosphinyl]choline hydroxide internal salt, O-[hydroxy-[3-[1-[(E)-stigmasta-5,22-dien-3β-yloxy]formamido]propoxy]phosphinyl]choline hydroxide internal salt, O-[hydroxy-[(RS)-3-[N-isopropyl-1-[(E)-stigmasta-5,22-dien-3β-yl]oxyformamido]-2-[(methylcarbamoyl)oxy]propoxy]phosphinyl]choline hydroxide internal salt, O-[[[2-[1-cholest-5-en-3β-yloxy]formamido]ethoxy]hydroxyphosphinyl]choline hydroxide internal salt, O-[[2-[1-(5β-cholestan-3α-yloxy)formamido]ethoxy]hydroxyphosphinyl]choline hydroxide internal salt, 1-[2-[[hydroxy-[3-[1-[(E)-stigmasta-5,22-dien-3β-yloxy]formamido]propoxy]phosphinyl]oxy]ethyl]pyridinium hydroxide internal salt, O-[hydroxy-[2-[[[(E)-stigmasta-5,22-dien-3β-yloxy]carbonyl]oxy]ethoxy]phosphinyl]choline hydroxide internal salt, 1-[2-[[[2-[1-[cholest-5-en-3β-yloxy]formamido]ethoxy]hydroxyphosphinyl]oxy]ethyl]-1-methylpyrrolidinium hydroxide internal salt, 1-O-(3α,β-stigmastanyl)-3-O-(RS)-glyceryl-phosphorylcholine, O-[[(RS)-2-acetoxy-3-[5α-stigmastan-3α,β-yloxy]propoxy]hydroxyphosphonyl]choline hydroxide internal salt, O-[[(RS)-3-[(cholest-5-en-3β-yloxy)carbonyloxy]-2-hydroxypropoxy]hydroxyphosphinyl]choline hydroxide internal salt, O-[hydroxy-(RS)-2-hydroxy-3-[[5α-stigmastan-3β-yloxy)carbonyloxy]propoxy]phosphinyl]choline hydroxide internal salt O-[hydroxy-[(RS)-2-hydroxy-3-[[(E)-stigmasta-5,22-dien-3β-yloxy]carbonyloxy]propoxy]phosphinyl]choline hydroxide internal salt, O-[hydroxy-[2-[[(stigmast-5-en-3β-yloxy)carbonyl]oxy]ethoxy]phosphinyl]choline hydroxide internal salt, O-[hydroxy-[3-[(stigmast-5-en-3β-yloxy)carbonyl]propoxy]-phosphinyl]choline hydroxide internal salt, O-[hydroxy-[2-(stigmast-5-en-3β-yloxy)ethoxy]phosphinyl]choline hydroxide internal salt, cholest-5-en-3β-yl 2-[[[2-(dimethylamino)ethoxy]hydroxyphosphinyl]oxy]ethylcarbonate, O-[hydroxy-[2-[1-(stigmast-5-en-3β-yloxy)formamido]ethoxy]phosphinyl]choline hydroxide internal salt, O-[[(RS)-2-acetoxy-3-[[(cholest-5-en-3β-yloxy)carbonyl]oxy]propoxy]hydroxyphosphinyl]choline hydroxide internal salt, O-[[2-[cholest-5-en-3β-yloxy)carbonyl]-2-methylpropoxy]hydroxyphosphinyl]-choline hydroxide internal salt and O-[[(RS)-2-[1-(cholest-5-en-3β-yloxy)formamido]-3hydroxypropoxy]hydroxyphosphinyl]choline hydroxide internal salt.

12. A pharmaceutical composition comprising an effective amount of a compound of the formula

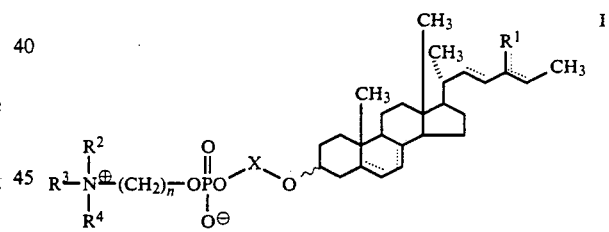

wherein
$R^1$ is hydrogen, lower-alkyl or lower-alkylidene,
$R^2$, $R^3$ and $R^4$ are hydrogen or lower-alkyl or together with the N atom form a 5- or 6-membered aromatic or saturated heterocyclic group which may be lower-alkylated,
n is the number 2, 3 or 4,
X is a group of the formula

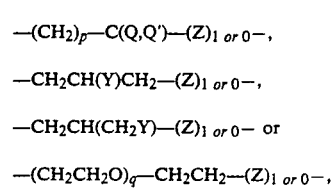

q is the number 1 or 2,
Z is a group of the formula —C(O)—, —OC(O)—, —OC(O)CH₂—, —OCH₂C(O)— or —N(T)-C(O)—, Q, Q' and T are hydrogen or lower-alkyl,
p is a whole number between 1 and 9 and, where Z is carbonyl, can also be O,
Y is hydroxy, lower-alkoxy, lower-alkanoyloxy, carbamoyloxy or mono- or di-lower alkyl-carbamoyloxy, wherein the dotted lines at the 5(6)-, 7(8)-positions can be a carbon to carbon bond, and up to one of the dotted lines at the 22(23)-, 24(25)- or 24(28)-positions can be a carbon to carbon bond,
and physiologically compatible salts thereof,
and an inert carrier.

13. A pharmaceutical composition in accordance with claim 12, wherein $R^1$ is hydrogen or lower-alkyl.

14. A pharmaceutical composition in accordance with claim 13, wherein $R^1$ is ethyl.

15. A pharmaceutical composition in accordance with claim 13, wherein $R^2$ is hydrogen or lower-alkyl and $R^3$ and $R^4$ are lower-alkyl.

16. A pharmaceutical composition in accordance with claim 15, wherein $R^2$, $R^3$ and $R^4$ are methyl.

17. A pharmaceutical composition in accordance with claim 13, wherein $R^2$, $R^3$ and $R^4$ together with the N atom form a pyridinium or 1-methylpyrrolidinium group.

18. A pharmaceutical composition in accordance with claim 12, wherein n is the number 2.

19. A pharmaceutical composition in accordance with claim 12, wherein the compound has a 5(6) unsaturated or 5(6)- and 20(23)-unsaturated steroid part.

20. A pharmaceutical composition in accordance with claim 12, wherein X is the group $-(CH_2)_2-$, $-(CH_2)_2O(CH_2)_2-$, $-(CH_2)_2O(CH_2)_2O(CH_2)_2-$, $-CH_2CHOHCH_2-$, $-CH_2CH(OCOCH_3)CH_2-$, $-CH_2CH(OCONHCH_3)CH_2N[CH(CH_3)_2]CO-$, $-(CH_2)_2NHCO-$, $-(CH_2)_3NHCO-$, $-CH_2CHOHCH_2OCO-$, $-(CH(CH_3)CO-$, $-(CH_2)_2OCO-$, $-(CH_2)_3OCO-$, $-(CH_2)_4OCO-$, $-(CH_2)_8OCO-$, $-(CH_2)CO-$, $-(CH_2)_2CO-$, $-(CH_2)_3CO-$, $-(CH_2)_5CO-$, $-CH_2CH(OCOCH_3)CH_2OCO-$, $-CH_2C(CH_3)_2CO-$ or $-CH_2CH(CH_2OH)NHCO-$.

21. A method of controlling or preventing hypercholesterolemia and atherosclerosis which comprises administering to a warm blooded animal an effective amount of a compound of the formula

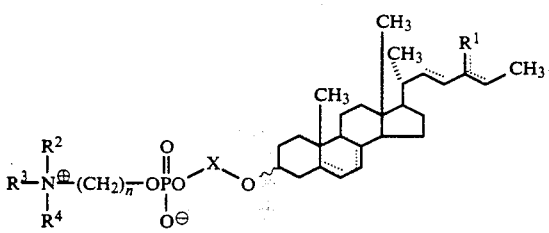

wherein
$R^1$ is hydrogen, lower-alkyl or lower-alkylidene,
$R^2$, $R^3$ and $R^4$ are hydrogen or lower-alkyl or together with the N atom form a 5- or 6-membered aromatic or saturated heterocyclic group which may be lower-alkylated,
n is the number 2, 3 or 4,
X is a group of the formula

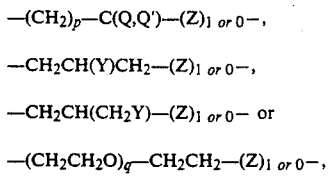

q is the number 1 or 2,
Z is a group of the formula $-C(O)-$, $-OC(O)-$, $-OC(O)CH_2-$, $-OCH_2C(O)-$ or $-N(T)-C(O)-$, Q, Q' and T are hydrogen or lower-alkyl, P is a whole number between 1 and 9 and, where Z is carbonyl, can be O, Y is hydroxy, lower—alkoxy, lower—alkanoyloxy, carbamoyloxy or mono- or di-lower alkyl-carbamoyloxy, wherein the dotted lines at the 5(6)-, 7(8)-positions can be a carbon to carbon bond, and up to one of the dotted lines at the 22(23)-, 24(25)- or 24(28)-positions can be a carbon to carbon bond,
and physiologically compatible salts thereof.

22. A method in accordance with claim 21, wherein $R^1$ is hydrogen or lower-alkyl.

23. A method in accordance with claim 22, wherein $R^1$ is ethyl.

24. A method in accordance with claim 22, wherein $R^2$ is hydrogen or lower-alkyl and $R^3$ and $R^4$ are lower-alkyl.

25. A method in accordance with claim 24, wherein $R^2$, $R^3$ and $R^4$ are methyl.

26. A method in accordance with claim 22, wherein $R^2$, $R^3$ and $R^4$ together with the N atom form a pyridinium or 1-methylpyrrolidinium group.

27. A method in accordance with claim 21, wherein n is the number 2.

28. A method in accordance with claim 21, wherein the compound has a 5(6) unsaturated or 5(6)-and 22(23)-unsaturated steroid part.

29. A method in accordance with claim 21, wherein X is the group $-(CH_2)_2-$, $-(CH_2)_2O(CH_2)_2-$, $-(CH_2)_2O(CH_2)_2O(CH_2)_2-$, $-CH_2CHOHCH_2-$, $-CH_2CH(OCOCH_3)CH_2-$, $-CH_2CH(OCONHCH_3)CH_2N[CH(CH_3)_2]CO-$, $-(CH_2)_2NHCO-$, $-(CH_2)_3NHCO-$, $-CH_2CHOHCH_2OCO-$, $-(CH(CH_3)CO-$, $-(CH_2)_2OCO-$, $-(CH_2)_3OCO-$, $-(CH_2)_4OCO-$, $-(CH_2)_8OCO-$, $-(CH_2)CO-$, $-(CH_2)_2CO-$, $-(CH_2)_3CO-$, $-(CH_2)_5CO-$, $-CH_2CH(OCOCH_3)CH_2OCO-$, $-CH_2C(CH_3)_2CO-$ or $-CH_2CH(CH_2OH)NHCO-$.

30. O-[hydroxy-[3-[(3β-stigmastanyloxy)carbonyl]-propoxy] phosphinyl]choline hydroxide internal salt.

31. The pharmaceutical composition of claim 12, wherein the compound of formula I is O-[hydroxy-[3-[(3β-stigmastanyloxy) carbonyl]-propoxy] phosphinyl]-choline hydroxide internal salt.

32. The method of claim 21, wherein the compound of formula I is O-[hydroxy-[3-[(3β-stigmastanyloxy) carbonyl]-propoxy] phosphinyl]choline hydroxide internal salt.

* * * * *